US010052464B2

United States Patent
Glynn (10) Patent No.: US 10,052,464 B2
(45) Date of Patent: *Aug. 21, 2018

(54) LOW FLOW RATE NASAL TREATMENT DELIVERY DEVICE FOR MIXED CARBON DIOXIDE AND SALINE

(71) Applicant: CLOVER HILL HEALTHCARE, INC., Flemington, NJ (US)

(72) Inventor: Kenneth P Glynn, Flemington, NJ (US)

(73) Assignee: CLOVER HILL HEALTHCARE, INC., Flemington, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 14/999,292

(22) Filed: Apr. 22, 2016

(65) Prior Publication Data

US 2016/0325080 A1    Nov. 10, 2016

Related U.S. Application Data

(63) Continuation-in-part of application No. 13/507,112, filed on Jun. 4, 2012, now Pat. No. 9,370,632.

(51) Int. Cl.
| | | |
|---|---|---|
| *A61M 31/00* | (2006.01) | |
| *A61M 39/24* | (2006.01) | |
| *A61M 3/00* | (2006.01) | |
| *A61M 11/00* | (2006.01) | |

(Continued)

(52) U.S. Cl.
CPC ............. *A61M 31/00* (2013.01); *A61K 33/00* (2013.01); *A61K 33/14* (2013.01); *A61M 3/005* (2013.01);

(Continued)

(58) Field of Classification Search
CPC ........ A61M 1/00; A61M 1/006; A61M 1/007; A61M 1/008; A61M 11/02; A61M 16/10;
(Continued)

(56) References Cited

U.S. PATENT DOCUMENTS

| | | |
|---|---|---|
| 5,609,581 A | 3/1997 | Fletcher et al. |
| 7,017,573 B1 * | 3/2006 | Rasor ............... A61H 33/14 |
| | | 128/200.24 |

(Continued)

OTHER PUBLICATIONS

Casale, et al., "Nasal Carbon Dioxide for the Symptomatic Treatment of Perennial Allergic Rhinitis" Date Published Oct. 2011, Ann Allergy Asthma Immunol., pp. 364-370.

(Continued)

*Primary Examiner* — Andrew Gilbert
*Assistant Examiner* — James D Ponton (57) ABSTRACT

A method of treatment and a nasal delivery device for dosages containing dissolved gaseous carbon dioxide in saline fluid for treating head ailments includes: a) a main housing having a hollow central area containing the dosage; b) a dosage dispenser head located at the distal end of the main housing, having at least one flow channel for movement of the dosage from the main housing through the dosage dispenser head and externally of the dosage dispenser head; c) a dosage release control component located between the main housing and the dosage dispenser head to permit flow of the dosage through the dosage dispenser head in response to increased pressure against the dosage at a flow rate of less than 1 cc per second; and d) a pressure-changing moveable component located on the main housing.

14 Claims, 9 Drawing Sheets

(51) Int. Cl.
*A61M 11/02* (2006.01)
*A61M 15/08* (2006.01)
*A61K 33/00* (2006.01)
*A61K 33/14* (2006.01)
*A61K 45/06* (2006.01)
*A61K 9/00* (2006.01)

(52) U.S. Cl.
CPC .......... *A61M 11/00* (2013.01); *A61M 11/007* (2014.02); *A61M 11/02* (2013.01); *A61M 15/08* (2013.01); *A61M 39/24* (2013.01); *A61K 9/0043* (2013.01); *A61K 45/06* (2013.01); *A61M 2202/0225* (2013.01); *A61M 2202/0468* (2013.01); *A61M 2205/3334* (2013.01)

(58) Field of Classification Search
CPC ...... A61M 2202/0225; A61M 15/0001; A61M 15/0003; A61M 15/0005; A61M 15/0065; A61M 15/08; A61M 16/12; A61M 16/14; A61M 31/00; A61M 3/005; A61M 2205/0225
See application file for complete search history.

(56) References Cited

U.S. PATENT DOCUMENTS

| | | | |
|---|---|---|---|
| 7,827,986 B2 | 11/2010 | Rasor et al. | |
| 7,836,883 B2 | 11/2010 | Rasor et al. | |
| 7,845,348 B2 | 12/2010 | Rasor et al. | |
| 7,858,650 B2 | 12/2010 | Yamamoto et al. | |
| 7,959,597 B2 | 6/2011 | Baker et al. | |
| 8,007,842 B2 | 8/2011 | Rau | |
| 2004/0009126 A1 | 1/2004 | Pilkiewicz et al. | |
| 2006/0172017 A1 | 8/2006 | Rasor et al. | |
| 2008/0029086 A1 | 2/2008 | Harlan et al. | |
| 2008/0066739 A1 | 3/2008 | LeMahieu et al. | |
| 2008/0066741 A1 | 3/2008 | LeMahieu et al. | |
| 2008/0078382 A1 | 4/2008 | LeMahieu et al. | |
| 2008/0114310 A1 | 5/2008 | Kamen et al. | |
| 2008/0169047 A1 | 7/2008 | Connolly et al. | |
| 2010/0305130 A1 | 12/2010 | Phillips et al. | |

OTHER PUBLICATIONS

Barody et al., "The Effect of Intranasal Carbon Dioxide on the Acute Response to Nasal Challenge with Allergen" Date Published May-Jun. 2011, Allergy Asthma Proc., pp. 206-212.

Pagani et al., "Carbon Dioxide-Enriched Water Inhalation in Patients With Allergic Rhinitis and its Relstionship with Nasal Fluid Cytokine/Chemokine Release" Date Published May 2011, Arch Med Res, pp. 329-333.

Casal, Romero, and Spierings, "Intranasal Noninhaled Carbon Dioxide for the Symptomatic Treatment of Seasonal Allergic Rhinitis" Date Published Jan. 2008, J Allergy Clin Immunol., pp. 105-109.

* cited by examiner

LOW FLOW RATE NASAL TREATMENT DELIVERY DEVICE FOR MIXED CARBON DIOXIDE AND SALINE

REFERENCE TO RELATED APPLICATIONS

The present application is a continuation-in-part application of copending U.S. patent application Ser. No. 13/507,112, by the same inventor herein, namely, Kenneth P. Glynn, filed on Jun. 4, 2012 titled "NASAL TREATMENT DELIVERY DEVICE FOR MIXED CARBON DIOXIDE AND SALINE TREATMENTS".

BACKGROUND OF INVENTION a. Field of Invention

The invention relates generally to healthcare, and specifically to the treatment of head ailments. More specifically, the present invention relates to intranasal delivery devices for treatments with mixtures of carbon dioxide and saline, as well as methods of treatment utilizing these devices.

b. Description of Related Art

The following patents and applications are representative of various types of nasal medicine delivery devices:

U.S. Pat. No. 8,007,842 B2 to Rau describes a composition for providing aromatherapy, and in particular, symptomatic relief of nasal and sinus congestion in unit dosage format. The composition includes a penetrating aromatic vapor whose release from a preparation of warm water is augmented by an effervescent component which reacts in the warm water to promote release of the aromatic fragrance, or sustained over time by tableting or gelatin encapsulation. As the fragrance is inhaled, symptomatic relief is obtained. The composition of matter may be rendered ingestible, so that the warm water containing the composition is consumed following inhalation. In preferred embodiments, the release of the penetrating aromatic fragrance persists over time.

U.S. Pat. No. 7,959,597 B2 to Baker et al. describes an irrigation and aspiration system. The system can be configured to aspirate and irrigate alone, sequentially or concurrently. The system can be configured to aspirate and irrigate the nasal cavity. The system can be manually controlled. The system can have removable and easily cleanable reservoirs for aspirant and irrigant.

U.S. Pat. No. 7,858,650 B2 to Yamamoto et al. describes a medicinal composition for inhalation containing a continuous-release type prodrug of an EP2 agonist which topically exhibits a prolonged bronchodilating and antiinflammatory effects. Namely, the medicinal composition for inhalation containing a continuous-release type prodrug of an EP2 agonist is useful as a safe preventive and/or a remedy for respiratory diseases (for example, asthma, pulmonary injury, pulmonary fibrosis, pulmonary emphysema, bronchitis, chronic obstructive pulmonary disease, adult respiratory distress syndrome, cystic fibrosis, pulmonary hypertension or the like) without causing any systemic effect such as lowering blood pressure. Thus, a safe and useful remedy for respiratory diseases is provided.

U.S. Pat. No. 7,845,348 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,836,883 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 7,827,986 B2 to Rasor et al. describes apparatus, methods, and kits for treating symptoms associated with common ailments, such as headaches, rhinitis, asthma, epilepsy, nervous disorders and the like. The apparatus comprises dispensers for carbon dioxide and other therapeutic gases. The methods comprise delivering small volumes of these gases to patients in a manner where the gas infuses into a body region in order to bathe the mucous membranes therein. It has been found that even very short exposure of patients to small volumes and high concentrations of such gases can provide significant relief from symptoms.

U.S. Pat. No. 5,609,581 to Fletcher, et al. describes the combination comprising a container for a product having a puncturable diaphragm at one end thereof, an applicator of elongated parabolic shape including means for detachably mounting it on the container, an internal piercing element in the applicator aligned with the diaphragm and a plurality of discharge openings in the applicator, the applicator actuatable between an unarmed position wherein the piercing element is spaced from the diaphragm in an armed position where it punctures the diaphragm to permit discharge of the contents through the piercing element and the discharge openings in the applicator.

United States Patent Application No. 2010/0305130 A1 to Phillips describes a single-use sprayer for nasal anesthesia is disclosed. The single-use sprayer includes a single dose of anesthetic and a delivery system adapted to dispense the single dose of anesthetic into a nostril. The single-use sprayer prevents patient-to-patient contamination, is easy to use and allows for self-administration, and has a simple, disposable configuration so as to lower the production cost.

United States Patent Application No. 2008/0169047 A1 to Connolly et al. describes a hand-held, low-flow dispenser which comprises an enclosure holding a gas cartridge. A spring-biased needle is advanced to puncture a septum on the gas cartridge, and a separate spring-biased ball valve is used to turn the resulting gas flow off and on as well as to control the flow rate.

United States Patent Application No. 2008/0114310 A1 to Kamen, et al. describes a method for packaging an agent for delivery within a body cavity. A reservoir within a package contains a specified quantity of the agent and is either contiguous with, or coupled to, a dispensing node such as a swab. Depth of insertion of the dispensing node into the body cavity is restricted to a specified depth by a penetration-restricting feature that forms part of the package.

United States Patent Application No. 2008/0078382 A1 to LeMahieu et al. describes systems and methods for delivery of a drug to the respiratory system of a patient in a stream of purified air are provided. In particular, the drugs are delivered to the respiratory system of the patient at a positive air pressure relative to atmospheric pressure. With the systems and methods of the present disclosure, medication available in a variety of forms is introduced in a controlled fashion into the air stream in aerosol, nebulized, or vaporized form.

United States Patent Application No. 2008/0066741 A1 to LeMahieu et al. describes systems and methods for delivery of a drug to the respiratory system of a patient, where the drug is supplied in purified air at a positive pressure relative to atmospheric pressure. With the systems and methods of the present disclosure, medication available in a variety of forms is introduced in a controlled fashion into the purified air stream in aerosol, nebulized, or vaporized form.

United States Patent Application No. 2008/0066739 A1 to LeMahieu et al. describes systems and methods for delivery of a drug to the respiratory system of a patient where the drug is supplied at a positive pressure relative to atmospheric pressure. In particular, the drugs are delivered to the respiratory system of a patient who is capable of unassisted breathing. With the systems and methods of the present disclosure, medication available in a variety of forms is introduced in a controlled fashion into the air stream in aerosol, nebulized, or vaporized form.

United States Patent Application No. 2008/0029086 A1 to Harlan, et al. describes a nasal passage washing device includes a pliable body including an open top; and an applicator cap removably attached to the pliable body to cover and uncover the open top. The applicator cap includes an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and a one-way air valve that only allows air flow into the pliable body through the one-way air valve and does not allow air flow and washing solution flow out of the pliable body through the one-way air valve.

United States Patent Application No. 2006/0172017 A1 to Rasor et al. describes an apparatus and methods to deliver vasoconstrictive agents simultaneously with capnic gases. The capnic gases can enhance the effectiveness of the vasoconstrictive agent, lower the dosage of drug or concentration of agent necessary to achieve a therapeutic result, or both. Exemplary capnic gases include carbon dioxide, nitric oxide, nitrous oxide, and dilute acid gases.

United States Patent Application No. 2004/0009126 A1 to Pilkiewicz et al. describes an inhalation system comprising an anti-infective agent in particle form, the anti-infective agent being directed toward prevention and treatment of intracellular infection, and an inhalation device, and a method of use of the system.

United States Patent Application No. 2002/0040205 A1 to Rasor et al. describes methods and devices for transcutaneous and transmucosal application of carbon dioxide in the form of gas and in the form of a capnic solution (such as carbonated water) for the relief of pain, including musculoskeletal disorders, neuralgias, rhinitis and other ailments. Gaseous carbon is applied to the skin for at least three minutes, and the capnic solution may be held on the skin for at least three minutes, which provides relief of symptoms. The capnic solution may be sprayed onto mucous membranes such as the nose for relief of symptoms such as allergic rhinitis.

Casale, et al., "Nasal Carbon Dioxide for the Symptomatic Treatment of Perennial Allergic Rhinitis," Ann Allergy Asthma Immunol., October 2011, pp. 364-370, examines the safety and efficacy of nasal carbon dioxide on the symptoms of perennial allergic rhinitis.

Baroody et al., "The Effect of Intranasal Carbon Dioxide on the Acute Response to Nasal Challenge with Allergen," Allergy Asthma Proc., May-June 2011, pp. 206-212 describes a study in which intranasal carbon dioxide (CO(2)) was shown to reduce symptoms of seasonal allergic rhinitis (SAR). This study was designed to evaluate the effect of CO(2) on nasal allergen challenge. We conducted a randomized, controlled, crossover trial in 12 subjects with SAR outside their pollen season. Thirty minutes after a 20-second exposure to CO(2) or no exposure, subjects underwent a unilateral, localized, nasal allergen challenge. Filter paper disks were placed on the nasal septum to deliver a sham challenge followed by 2 increasing doses of either grass or ragweed allergen. Secretions were collected from both sides of the septum to evaluate the nasonasal reflex and were assayed for histamine. Nasal and eye symptoms were recorded. The primary outcome measure was the contralateral, reflex, secretory response to allergen as measured by secretion weights. Secondary outcome measures included ipsilateral nasal secretion weights, nasal and eye symptoms, levels of histamine in nasal secretions, and eosinophils in nasal scrapings. Subjects reported a transient burning sensation during exposure to CO(2). Compared with no treatment, active treatment resulted in a significant reduction in sneezes (p=0.05), contralateral secretion weights (p=0.04), and bilateral runny nose symptoms (p=0.01). Ipsilateral secretion weights were numerically reduced. Histamine levels in ipsilateral nasal secretions increased significantly when the subjects received sham treatment but did not increase after pretreatment with CO(2). Treatment with nasal CO(2) resulted in partial reduction of the acute response to allergen challenge. Reflex responses were reduced, supporting an effect on neuronal mechanisms, which predict usefulness in the treatment of allergic rhinitis.

Pagani et al., "Carbon Dioxide-Enriched Water Inhalation in Patients With Allergic Rhinitis and its Relationship with Nasal Fluid Cytokine/Chemokine Release," Arch Med Res, May 2011, pp. 329-333 investigates a possible in vivo effect of carbon dioxide-enriched water inhalation in patients with allergic rhinitis.

Casale, Romero, and Spierings, "Intranasal Noninhaled Carbon Dioxide for the Symptomatic Treatment of Seasonal Allergic Rhinitis," J Allergy Clin Immunol., January 2008, pp. 105-109, studies whether noninhaled intranasal CO2 would be effective in the treatment of seasonal allergic rhinitis.

Notwithstanding the prior art, the present invention is neither taught nor rendered obvious thereby.

SUMMARY OF INVENTION

The present invention is directed to a nasal treatment delivery device for mixed carbon dioxide and saline for treating head ailments in a patient in need thereof, comprising: a) a main housing having a proximal and a distal end and having a hollow central area containing a dosage that includes a saline fluid and a gas containing carbon dioxide; b) a dosage dispenser head located at the distal end of the main housing, the dosage dispenser head having at least one flow channel for movement of the dosage from the main housing through the dosage dispenser head and to external of the dosage dispenser head; c) a dosage release control component located between the main housing and the dosage dispenser head adapted to permit flow of the dosage from the main housing and through the dosage dispenser head in response to increased pressure against the dosage, at a flow rate not to exceed 1 cc per second and preferably less than 1 cc per second, based on the total flow rate of the dosage; and d) a pressure-changing moveable component located on the main housing. When the dosage dispenser head of the device is placed in a nasal cavity and the pressure-changing moveable component is activated by movement toward the dosage, the dosage is at least partially forced through the dosage release control component and through the dosage dispenser head for application of the dosage to a nasal cavity wall.

In some embodiments of the present invention releasable nasal treatment delivery device, the flow rate is in the range of 0.01 to 1 cubic centimeter per second. In some preferred embodiments, the flow rate is in the range of 0.08 to 1 cubic centimeter per second. In some more preferred embodiments, the releasable nasal treatment delivery device flow rate is in the range of 0.1 to 1 cubic centimeter per second.

In some embodiments of the present invention releasable nasal treatment delivery device, the dosage release control component is selected from the group consisting of a frangible member, a puncturable member and a one-way valve.

In some embodiments of the present invention releasable nasal treatment delivery device, the main housing is an open ended tube with said dosage release control component and said dosage dispenser head are located at said distal end of said main housing and said pressure-changing moveable component is located at said proximal end of said main housing.

In some embodiments of the present invention releasable nasal treatment delivery device, the pressure-changing moveable component is a flexible squeeze member and a seal float.

In some embodiments of the present invention releasable nasal treatment delivery device, the pressure-changing moveable component is a push-up piston.

In some embodiments of the present invention releasable nasal treatment delivery device, the main housing is a tube having an open distal end and a closed proximal end, with said dosage release control component and said dosage dispenser head are located at said distal end of said main housing, and at least a portion of said tube is flexible and constitutes said pressure-changing moveable component.

In some embodiments of the present invention releasable nasal treatment delivery device, the releasable nasal treatment delivery device further comprises a nose guard flange connected to and extending from at least one of said main housing and said dosage dispenser head.

Other embodiments of the present invention involve methods of treating head ailments in a patient in need thereof utilizing the present invention nasal treatment delivery device described above. Thus, the present invention is also directed to the aforesaid method of treating, which comprises: a) providing the releasable nasal treatment delivery device described above; and, b) directing at least a portion of the nasal treatment dosage of the device described above to at least one nasal cavity of said patient through the flow regulating device. In some of these present invention methods, the flow regulating device of the releasable nasal treatment delivery device is set to deliver at a flow rate in the range of 0.01 to 1 cubic centimeter per second. In some preferred embodiments of the present invention methods, the flow regulating device of the releasable nasal treatment delivery device is set to deliver at a flow rate is in the range of 0.08 to 1 cubic centimeter per second. In some most preferred embodiments of the present invention methods, the flow regulating device of the releasable nasal treatment delivery device is set to deliver at a flow rate is in the range of 0.1 to 1 cubic centimeter per second. Ranges of 0.2 to 0.8 cc per second are optimal for some treated head ailment conditions.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE EMBODIMENTS

"Saline" and "saline solution" as used herein means water containing salt. Saline solutions are used in a wide variety of medical applications. For example, "normal saline" is the commonly used term for a solution of 0.90% w/v of sodium chloride (NaCl). Normal saline is frequently used in intravenous drips for patients unable to take fluids orally to prevent dehydration. Normal saline is also used to flush wounds and skin abrasions. Another application of saline solution is as a rinse for contact lenses.

Saline solution also is frequently used in nasal washes to treat some of the symptoms of the common cold or other ailments adversely affecting the nasal cavities. By irrigating the nasal passages with saline, inflammation can be reduced. Also, more concentrated ("hypertonic") solutions of NaCl, can have therapeutic uses. For example, 7% NaCl/water solutions are considered mucoactive agents and as such are used to hydrate thick secretions (mucous) in order to make it easier to cough up and out (expectorate).

Another chemical substance useful in medical treatments is carbon dioxide. One example is the use of diluted carbon dioxide by inhalation for treating symptoms related to headaches, allergies, asthma, nervous disorders, and other common ailments, which was demonstrated in the 1940s and 1950s. Another example is the use of high-concentration, non-inhaled carbon dioxide, delivered to the nasal passages locally. This type of treatment may provide fast relief without the adverse side effects of systemic drugs that are inhaled, ingested, or injected.

By combining the beneficial therapeutic effects of saline treatment and carbon dioxide treatment, an improved and synergistic therapy is created. In this way, the beneficial effects of the saline, such as reduced inflammation and expectoration of mucous, are combined with the beneficial effects of carbon dioxide therapy, such as relief from headaches, allergies, asthma, nervous disorders, and other common ailments. Further, the saline moisturizes the nasal cavities and acts as a base host for the carbon dioxide as it acts on the nasal cavity walls. (It is hypothesized that at least some of the carbon dioxide is adsorbed by the saline.) In addition, the saline reduces any slight burning that might otherwise be felt from the carbon dioxide. In this way, the benefits of saline treatment are supplemented by the benefits of carbon dioxide treatment, and the benefits of carbon dioxide treatment are supplemented by the benefits of saline treatment. This combination of utilizing the saline to perform at least moisturizing and other beneficial affects while carrying and enhancing the delivery of the carbon dioxide is an unexpected synergistic result thereof. It is seen that the gaseous carbon dioxide is at least partially dissolved, or fully dissolved, in the saline.

In addition to the benefits listed above, the present invention device using low flow rate dissolved gaseous carbon dioxide and saline nasal delivery methods and treatments have other synergistic benefits that are not available from either saline treatment or carbon dioxide treatment alone. For example, the presence of dissolved carbon dioxide in the saline solution means that the solution will be carbonated; the effervescent effect of the carbon dioxide helps the saline solution to mix more energetically against the interior surface of the nasal cavity or cavities. This improved mixing allows the saline treatment to be more effective. Another potential advantage of combining carbon dioxide and saline treatments is that in some embodiments, with sufficient pressure and a proper nozzle, the carbon dioxide can act as a carrier gas for the saline, allowing the saline solution to be aerosolized.

To summarize the advantages and benefits of the present invention, the combination of controlled delivery carbon dioxide and saline provides the following: it cleanses the nasal cavity removing allergens and particulates that cause inflammation and congestion; its special formula shields nasal mucosa from viruses; it soothes and moisturizes irritated mucosa; its unique buffering system neutralizes inhaled irritants such as oxidative free radicals and endogenous cytotoxins which cause inflammation and damage to the sensitive mucosa and muco-cillary hairs in the nasal cavity; it enhances mucous clearance and flow by reducing mucus viscosity; its superior safety profile gives it broader application than corticosteroids and decongestants and can be used safely in children 6 months of age and adults, even with co-morbidities such as diabetes, hypertension, suppressed immune systems and pregnant and nursing females; and its exceptional safety profile allows for flexible dosing.

Referring now in detail to the drawings wherein like reference numerals designate corresponding parts throughout the several views, various embodiments of the present invention are shown.

Figure 1:
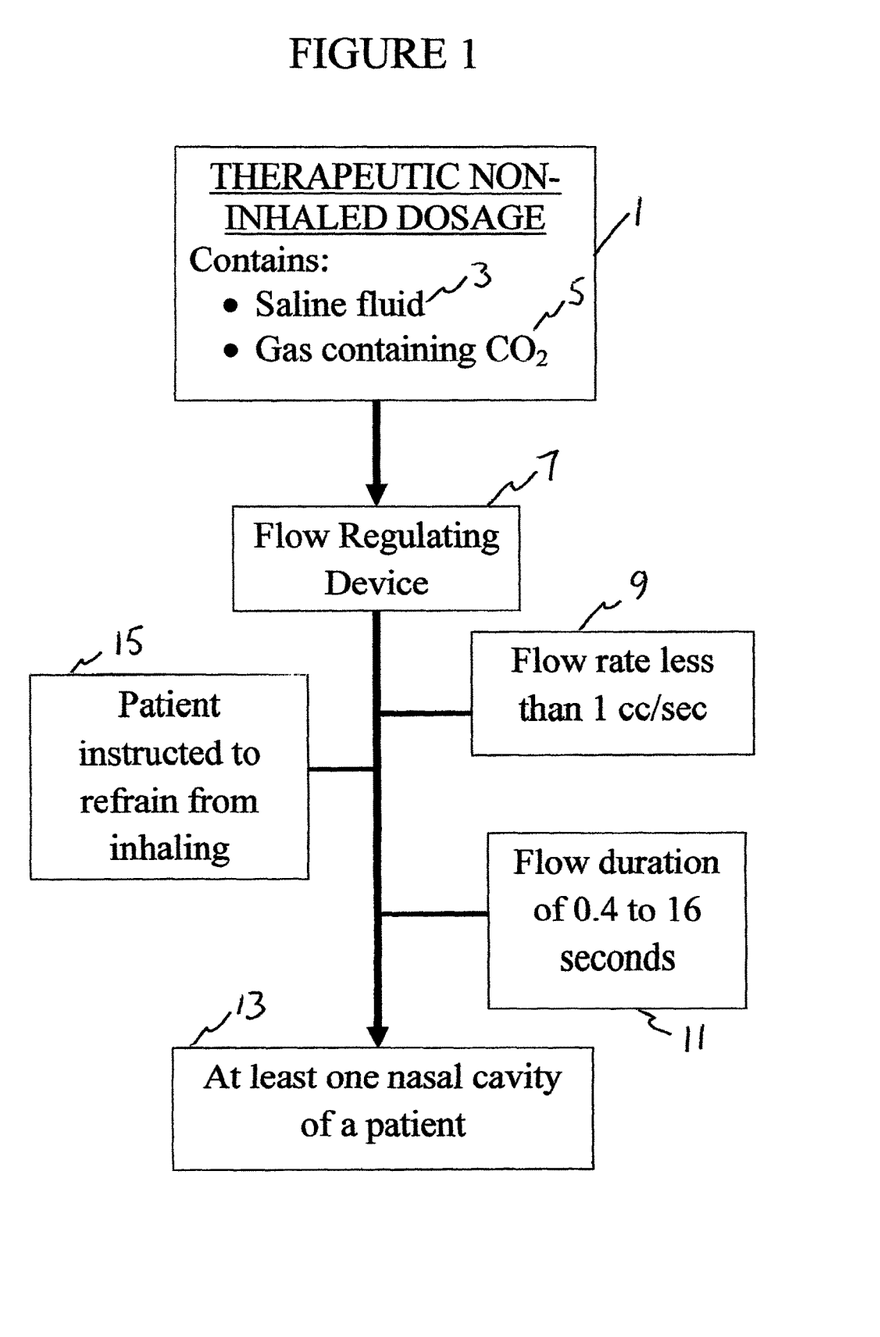
FIG. 1 is a block diagram of an embodiment of the present invention low flow rate device carbon dioxide and saline nasal delivery methods and treatments.

FIG. 1 is a block diagram of an embodiment of the present invention low flow rate device carbon dioxide and saline nasal delivery methods and treatments. FIG. 1 illustrates a therapeutic non-inhaled dosage 1 containing saline fluid 3 and a gas 5. Other constituents may be included The gas 5 includes carbon dioxide and is most preferably only carbon dioxide, dissolved in the saline fluid. The saline fluid 3 contains water and at least one salt. In some preferred embodiments of the present invention, the salt is sodium chloride. In other embodiments of the present invention, other salts may be used, but it is important that any salt used in the saline fluid 3 must be safe for intranasal use. In some preferred embodiments of the present invention, the concentration of salt in the saline fluid is approximately isotonic with the salt concentration of bodily fluids. In other preferred embodiments, the concentration of salt in the saline fluid is less than the concentration of salt in bodily fluids. In still other preferred embodiments, the concentration of salt in the saline fluid is hypertonic, meaning that it has a salt concentration higher than that of bodily fluids. In still other preferred embodiments, the saline solution is saturated with salt.

The gas 5 contains some portion of carbon dioxide. When the gas 5 containing carbon dioxide is added to the saline fluid 3, the saline fluid 3 becomes carbonated. If the therapeutic non-inhaled dosage 1 containing saline fluid 3 and the gas 5 is kept under pressure, the pressure can later be released (for example by opening a valve), which causes some of the carbon dioxide to bubble out of the solution. This sudden release of carbon dioxide creates effervescence in the therapeutic non-inhaled dosage.

The therapeutic non-inhaled dosage travels through a flow-regulating device 7. In preferred embodiments, the flow-regulating device 7 controls the flow rate 9 of the therapeutic non-inhaled dosage 1 at a rate that is safe and comfortable for the patient. In the embodiment shown in FIG. 1, the flow rate 9 of the therapeutic non-inhaled dosage is a low flow rate of less than 1 cubic centimeter per second (cc/sec). In preferred embodiments of the present invention shown in FIG. 1, the flow rate is adjustable to any value below 1 cc/sec that will provide some efficacy. This is discussed in further detail below.

The therapeutic non-inhaled dosage 1 has a flow duration 11. The flow duration 11 is the length of time during which the therapeutic non-inhaled dosage flows through the flow regulating device into at least one nasal cavity 13 of a patient. In the embodiment shown in FIG. 1, the flow duration 11 is shown as lasting between 0.4 and 16 seconds, inclusive. In preferred embodiments of the present invention, the flow duration is adjustable to any value between 0.4 and 16 seconds.

Figure 2:
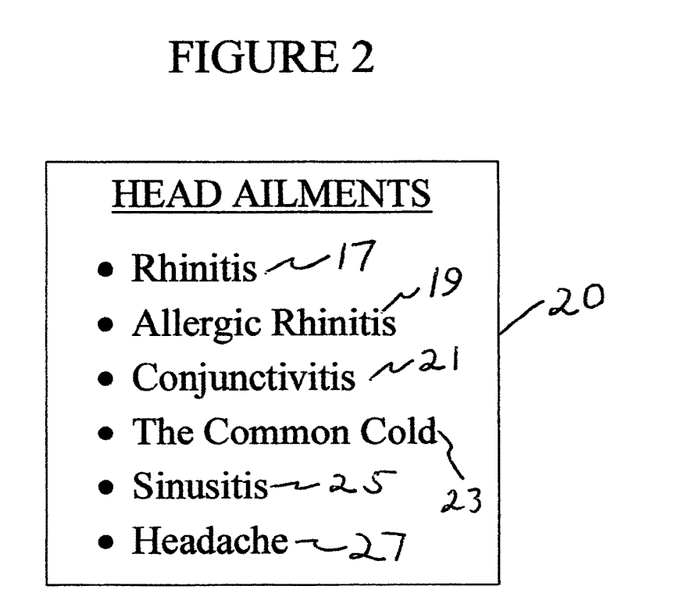
FIG. 2 is a block diagram showing head ailments treated by various embodiments of the present invention low flow rate carbon dioxide and saline nasal delivery devices.

After the therapeutic non-inhaled dosage 1 leaves the flow regulating device 7, it enters at least one nasal cavity 13 of a patient. The therapeutic non-inhaled dosage 1 is adsorbed by the nasal tissue and subsequently absorbed by the body. This adsorption and subsequent absorption can have a beneficial effect on many head ailments, some of which are shown in FIG. 2. The effervescent effect of the gas 5 containing carbon dioxide causes better contact between the salt in the saline solution 3 and the nasal tissue.

An optional additional step of instructing the patient to refrain from inhaling 15 protects the patient from accidently inhaling the therapeutic non-inhaled dosage 1. This is important, for a number of reasons, and one is that if the user inhales, some of the dosage bypasses the nasal cavity where it is most effective if left to dwell there. However, holding one's breathe is not essential, but preferred. Also, when the concentration of salt in the saline solution 3 is greater than isotonic (particularly if salts other than sodium chloride are used), it is desirable to limit the patient's exposure to the salts. The step 15 of instructing the patient not to breathe accomplishes these goals.

Turning now to FIG. 2, a block diagram, block 20, shows some of the medical conditions that can be treated using the present invention device with carbon dioxide and saline nasal delivery methods and treatments. In some embodiments of the present invention, the carbon dioxide and saline nasal delivery methods and treatments treat rhinitis 17, a swelling of some internal parts of the nose. In other embodiments, the present invention treats allergic rhinitis 19. In still other embodiments, the present invention treats conjunctivitis 21, an inflammation of the conjunctiva also known as pink-eye. In still other embodiments of the present invention, the common cold 23 is treated. In other embodiments of the present invention, sinusitis 25, an inflammation of the sinuses, is treated. In yet other embodiments, the present invention is used to treat headaches 27. It is important to recognize that in some embodiments of the present invention carbon dioxide and saline nasal delivery methods and treatments, multiple conditions can be treated simultaneously. For example, a patient may be suffering from both sinusitis and headache simultaneously; the present invention can alleviate both conditions at the same time. The present invention can treat any ailment shown in FIG. 2 or any combination of those ailments. It should also be recognized that the present invention may be useful in treating other ailments, particularly head ailments. The treatment of other ailments on which the present invention carbon dioxide and saline nasal delivery methods and treatments is effective are considered to be within the scope of the invention.

Figure 3:
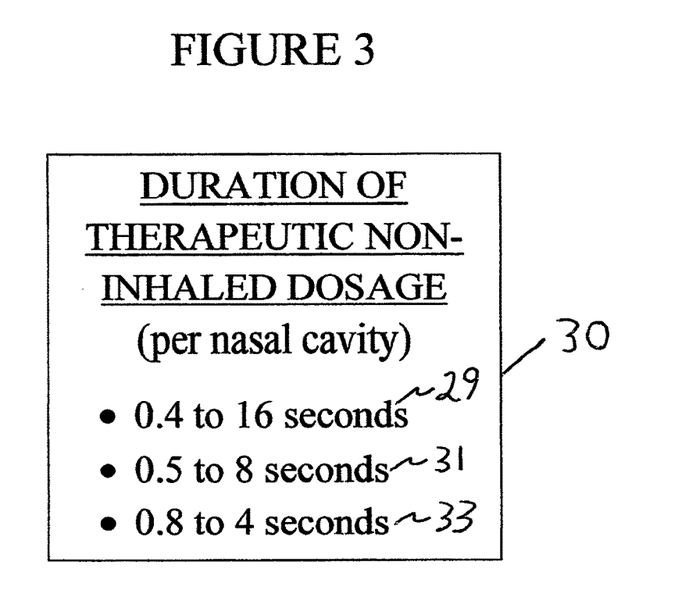
FIG. 3 is a block diagram showing durations for therapeutic non-inhaled dosage in some preferred embodiments of the present invention low flow rate carbon dioxide and saline nasal delivery devices.

Turning now to FIG. 3, a block diagram, block 30, shows the durations of therapeutic non-inhaled dosage used in some embodiments of the present invention carbon dioxide and saline nasal delivery methods and treatments. The durations listed in FIG. 3 are ranges, so the actual duration can be any value between the low end of the range and the high end of the range, inclusive. In some embodiments of the present invention, the duration 29 lasts between 0.4 and 16 seconds. In other embodiments of the present invention, the duration 31 lasts between 0.5 and 8 seconds. In still other embodiments of the present invention, the duration 33 lasts between 0.8 and 4 ten seconds. Durations of less than 0.4 seconds and more than 16 seconds are also considered to be within the scope of the invention.

Figure 4:
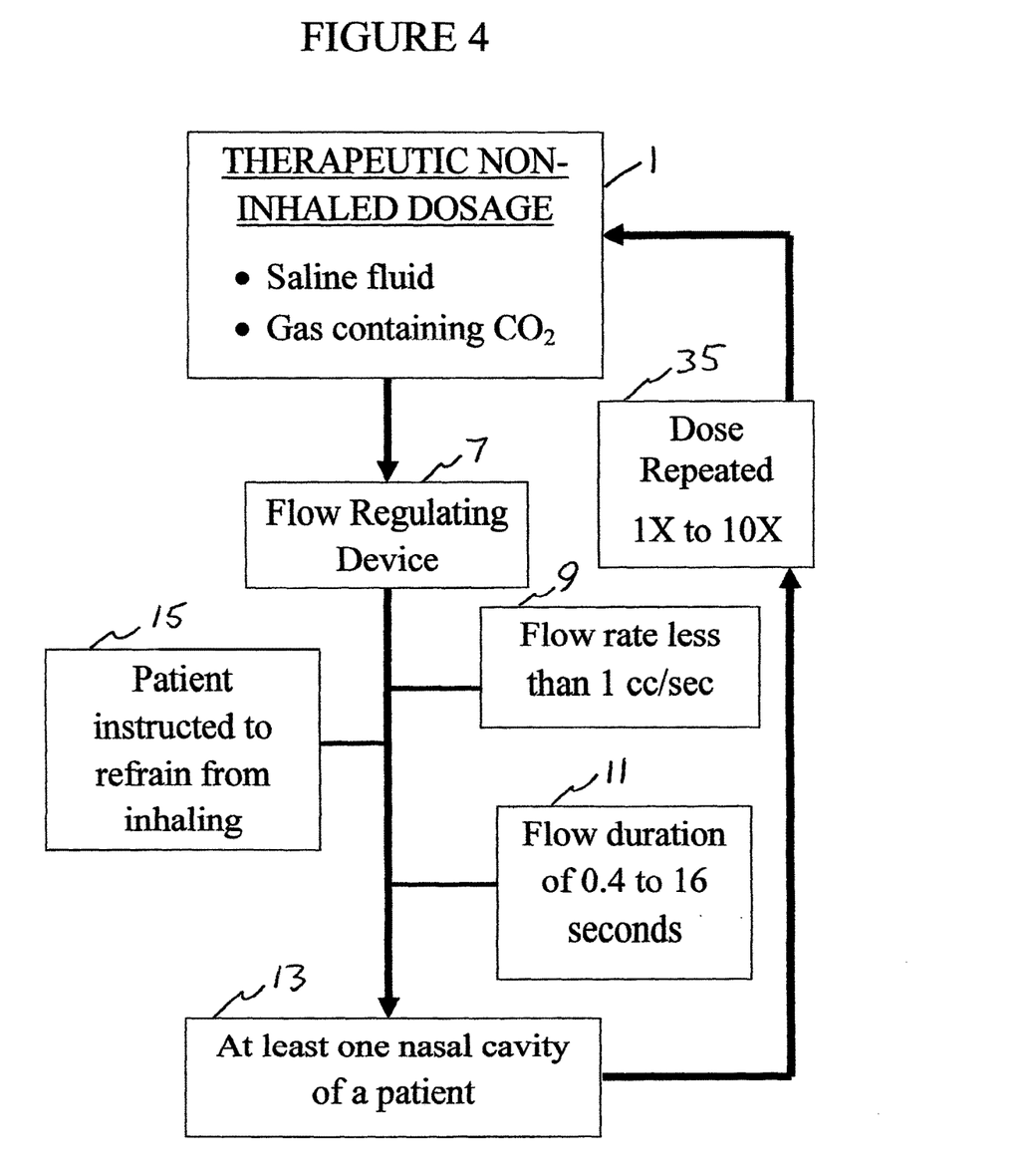
FIG. 4 is a block diagram of another embodiment of the present invention low flow rate device carbon dioxide and saline nasal delivery methods and treatments, showing the additional step of repeating the other steps.

FIG. 4 shows another embodiment of the present invention device carbon dioxide and saline nasal delivery methods and treatments. FIG. 4 is a block diagram that incorporates many aspects shown in FIG. 1, and identical blocks are identically numbered. In the embodiment shown in FIG. 4, after the therapeutic non-inhaled dosage 1 passes through the flow regulating device 7 and into the at least one nasal cavity 13 of a patient, the dose is repeated 35. In some preferred embodiments, the dose is repeated 35 between one and ten times. In still other embodiments, the dose is not repeated or repeated only once. While it is shown here that multiple repeat dosages can be administered, it is preferred that single doses be administered for normal use. The step 35 of repeating the dose can be used if a single application of the therapeutic non-inhaled dosage 1 is insufficient to alleviate the head ailment or ailments from which the patient suffers.

Figure 5:
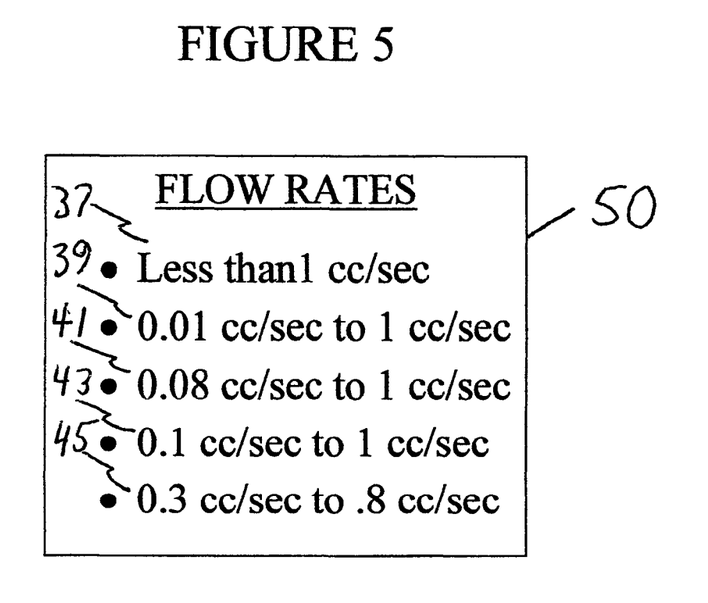
FIG. 5 is a block diagram showing flow rates in some preferred embodiments of the present invention low flow rate device carbon dioxide and saline nasal delivery methods and treatments.

Turning now to FIG. 5, a block diagram, block 50, shows flow rates used in some embodiments of the present invention device carbon dioxide and saline nasal delivery methods and treatments. The flow rates used in FIG. 5 are shown as ranges, and the actual rate of the flow may any value between the low end of the range and the high end of the range, inclusive. In some embodiments, a rate 37 less than 1 cc/sec is used. In other embodiments, a flow rate 39 between 0.01 cc/sec and less than 1 cc/sec is used. In other preferred embodiments, a flow rate 41 between 0.08 cc/sec and up to (less than) 1 cc/sec is used. In still other preferred embodiments, a flow rate 43 between 0.1 cc/sec and up to 1 cc/sec is used. In still other preferred embodiments, a flow rate 45 of 0.3 to 0.8 cc/sec is used.

Figure 6:
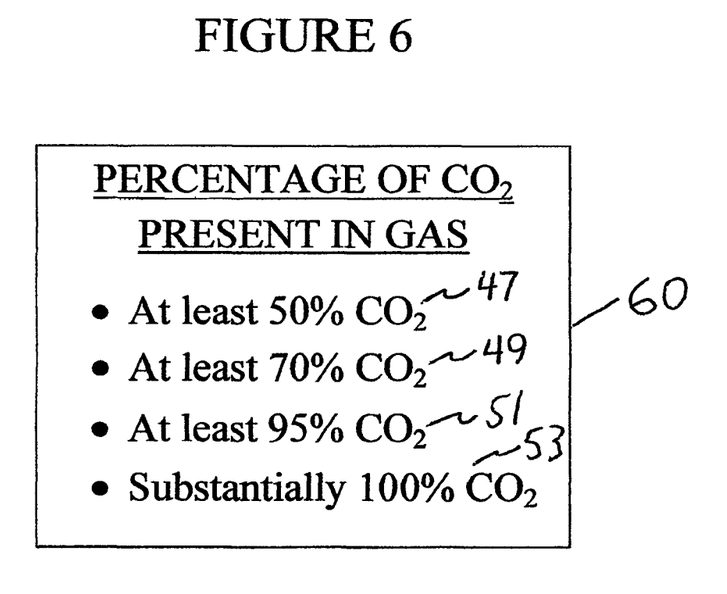
FIG. 6 is a block diagram showing the percentage of carbon dioxide present in the gas in some additional preferred embodiments of the present invention low flow rate device carbon dioxide and saline nasal delivery methods and treatments; and, FIG. 7 illustrates a diagrammatic view of various present invention low flow rate nasal treatment delivery device components and options.

Turning now to FIG. 6, a block diagram, block 60, shows levels of carbon dioxide in the gases used in some embodiments of the present invention devices. The levels of carbon dioxide are expressed as a percentage of the gas (3 in FIGS. 1 and 4) used in the therapeutic non-inhaled dosage (1 in FIGS. 1 and 4). In some embodiments of the present invention carbon dioxide and saline nasal delivery methods and treatments, the amount of carbon dioxide 47 in the gas is at least 50%. In other embodiments, the amount of carbon dioxide 49 in the gas is at least 70%. In still other embodiments, the amount of carbon dioxide 51 in the gas is at least 95%. In other preferred embodiments, the amount of carbon dioxide 53 in the gas is substantially 100%. Gases with a percent composition of less than 50% carbon dioxide are also considered to be within the scope of the invention.

Figure 7:
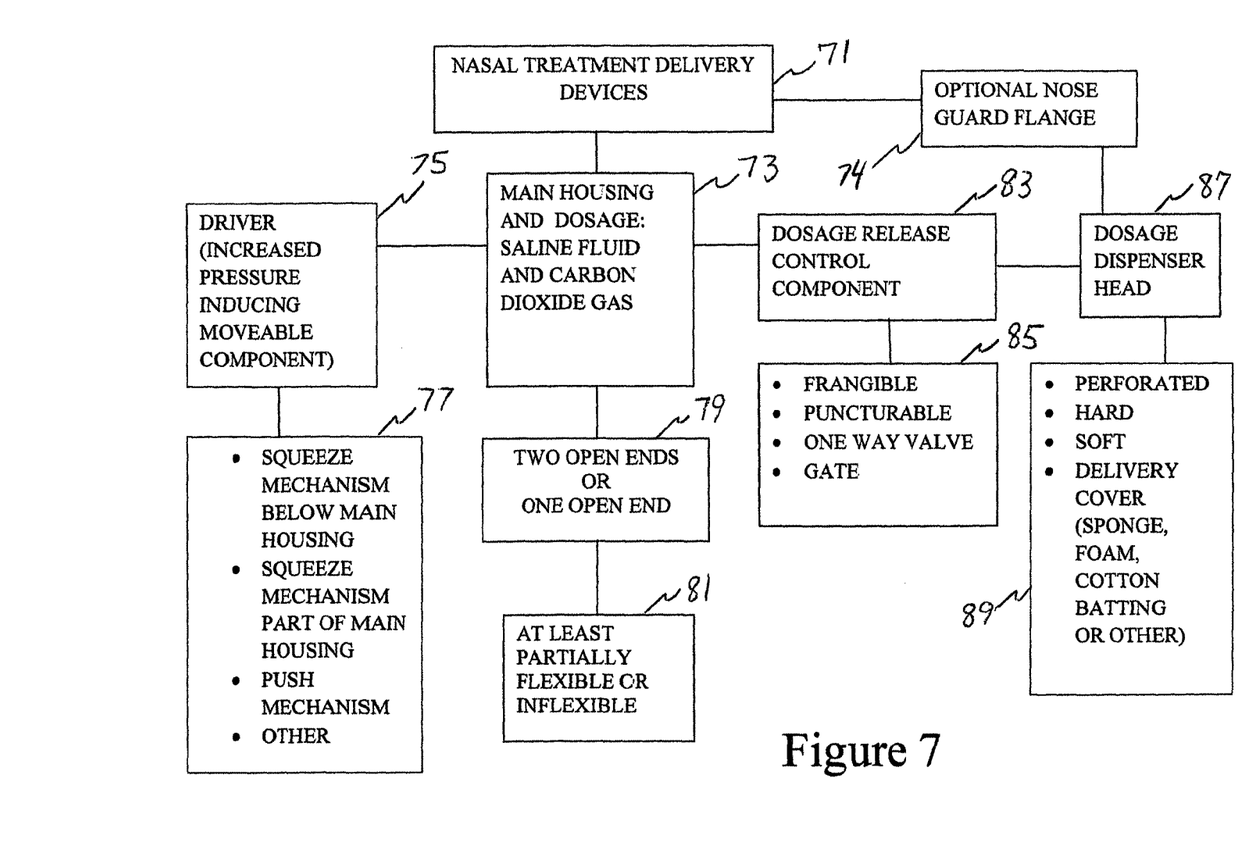

FIG. 7 illustrates a block diagram showing nasal treatment delivery devices that may be used in the present invention methods. Here, block 71 illustrates the caption of the Figure, namely, nasal treatment delivery device. The present invention device 71 may be a single dose dispenser (monodose) with a pressure control valve for flow rate regulation. The rate of flow is set in accordance with the ranges set forth above. In the case of a monodose dispenser, the entire dose is dispensed, so that time of dispensing does not need to be controlled—it is just the controlled flow rate over time it takes to unload the dose. Thus, a monodose dispenser may controllably release a pressurized mixture of the carbon dioxide and the saline, until it stops flowing. On the other hand, a plural or multidose dispenser may be used, and needs dispensing on/off control such as a spring return push mechanism/valve, otherwise the entire contents could be unnecessarily released in one shot.

The various types of mechanisms for driving the contents from the container to the nasal cavity are represented as driver 75 and block 77 provides specific examples. These include squeeze mechanisms where the squeeze component or bulb is below the content so that external squeeze pressure forces out the content, much like a turkey baster; squeeze mechanisms where the squeeze component is the actual dose holding aspect of the container, like a nasal decongestant squeeze spray container (these may require breakable seals); push mechanisms that physically operate much like syringes but may have more complex internal aspects, such as piercers or counter-biased valving; and others, referring to any known controlled flow mechanism available to the artisan, e.g., a pressurized container with a push release mechanism, including, but not limited to, pressurized bag-on-valve containers with one way valves.

In FIG. 7, block 73 shows the main housing and dosage. It contains a dosage of saline fluid and carbon dioxide gas according to parameters as more specifically set forth above. Block 79 shows that the main housing 73 may have two open ends or one open end. In the case of one open end, the top end would include the release control and dispenser head mechanisms, with a closed bottom. In the case of a main housing with two open ends, one end would have the release control and dispenser head mechanisms and the other end would contain a moveable drive mechanism such as a pressure release mechanism, a piercer or a plunger (drive piston). Block 81 shows that the main housing 73 may be at least partially flexible or it may be inflexible. If the driver is the squeezing of the main housing, it must be flexible. If the driver a moveable component attached to the main housing 71 (a push or squeeze mechanism), then the main housing 71 is preferably inflexible.

Block 83 shows the dosage release control component. Block 85 illustrates the options for the dosage release control component, which are: frangible, puncturable, one-way valve, or gate. A good example would be the afore-mentioned bag-on-valve container with a one way valve. Block 87 shows the dosage dispenser head, which Block 89 then shows the options for, which are: perforated, hard, soft, or delivery cover (sponge, foam, cotton batting, or other). Block 74 shows the optional nose guard flange for the nasal treatment delivery device 71.

Figure 8:
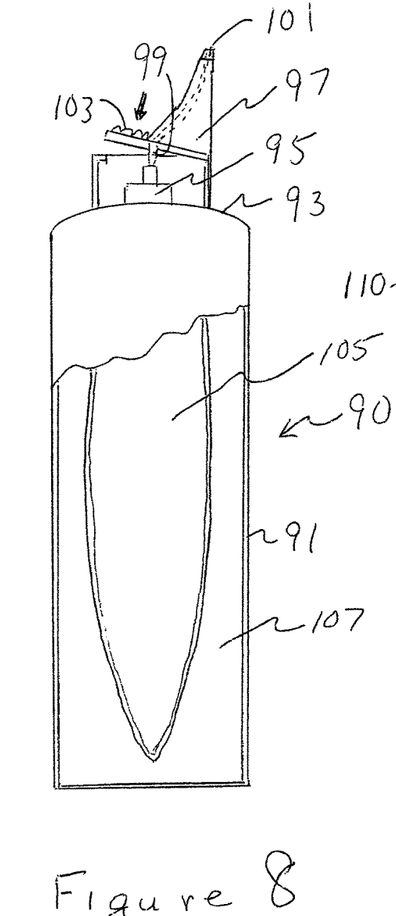
FIG. 8 illustrates a front partially cut view of one embodiment of a present invention low flow rate nasal treatment delivery device with a pressure release mechanism.

FIG. 8 illustrates a front partially cut view of one embodiment of a present invention nasal treatment delivery device 90. It includes a main housing 91 with a top 93 having a hollow central area containing a dosage of the present invention medicine. This storage area may be the inside of the main housing, or it may be one or more subunits-compartments, capsules, tanks, pouches, etc, within the main housing.

In this embodiment, the main housing 91 has attached to its distal end a dosage control component that is a spray release nozzle 95 that is set for prescribed flow rates within the ranges set forth in the present invention claims and as described above. Internal bag container 105 contains the liquid/gas mixture of the present invention and external pressure on bag 105 is created by pressurized gas located in space 107 inside main housing 91. At top 93 is a dosage dispenser head, in this case, a push dispenser mechanism 97 that includes release orifice 101, actuation tube 99 and push pad 103. A user inserts push dispenser mechanism 97 into a nasal cavity at its distal end (orifice 101) while holding nasal treatment delivery device 90 and then pressing push pad 103 to release the contents. The flow regulation is set to an acceptable range so as to be relatively gentle to the user. This may include ranges in the order of 1 cc/sec to 10 cc per second. Typically this is a multidose device wherein the user is given instructions to dispense for a specified time period while not breathing, e.g., three seconds at full depression per nostril twice a day as needed. Alternatively, a built-in timer could automatically control the dose. For example, the device could have a slow spring closure that would require reset and re-push to reactivate.

Figure 9:
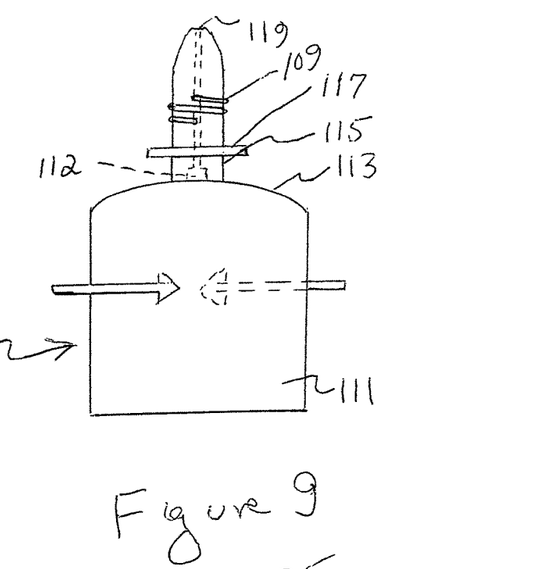
FIG. 9 illustrates a view of one embodiment of a present invention low flow rate nasal treatment delivery device that is a squeeze to release device.

FIG. 9 shows an alternative nasal treatment delivery device 110. This is an insert and squeeze device that includes a main body 111 with flexible walls and a dispensing nozzle 115 at its top 113. There is a stop 117 and threads 109 and a tapered dispensing tip 119 designed for nasal cavity insertion. There is a flow control valve 112 that regulates the rate of delivery. Additional valving, such as a duck bill valve, may also be included. The present invention liquid/gas mixture is contained within the main housing 111 and is dispensed by a user inserting and squeezing while holding his/her breath.

Figure 10:
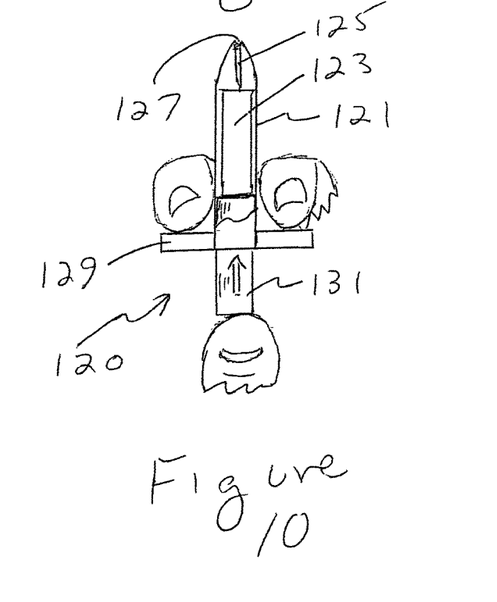
FIG. 10 shows a front partially cut view of a present invention low flow rate nasal treatment delivery device with a piercing channel, with the device being held in a hand using two fingers and a thumb to activate release of the medicinal treatment.

FIG. 10 shows a front partially cut view of a present invention nasal treatment delivery device 120 being held in a hand using two fingers and a thumb, as shown. There is a main housing 121 and a vertically moveable piston 131. A rigid, semi-flexible or flexible container or pouch 123 contains the liquid/gas mixture of the present invention and piercing tube 125 is connected to flow control valve 127. A user holds nasal treatment delivery device 120 as shown, inserts it into a nasal cavity, and while not breathing, pushes piston 131 upwardly to force pouch 123 to rupture via piercing tube 125 for medicine release through valve 127 to the nasal cavity walls.

Figures 11, 12:
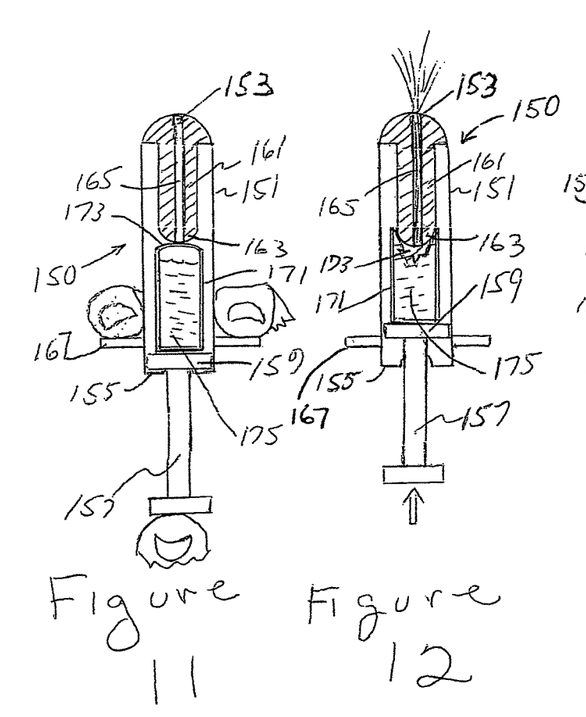
FIGS. 11, 12 and 13 illustrate front partially cut views of one embodiment of a present invention low flow rate nasal treatment delivery device with a frangible internal medicine capsule that may be used for a monodose or multidose using replacement cartridges. The three Figures show the device in different stages of use.
Figure 13:
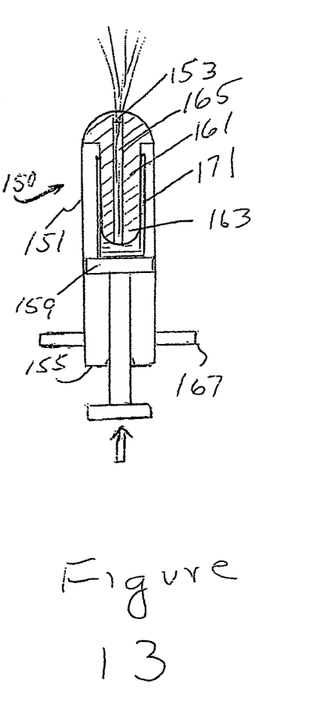

FIGS. 11, 12 and 13 illustrate front partially cut views of one embodiment of a present invention nasal treatment delivery device 150 with a frangible internal medicine capsule 171 containing medicine 175—the gas and liquid mixtures described above. Device 150 may be used for a monodose or multidose using replacement capsules. The three Figures show the device in different stages of use. Identical number is used for all three of the figures and the device 150 is described collectively for all of these figures.

Device 150 is a push device that relies upon a frangible capsule 171 to deliver the medicine 175 by breaking open the top 173 of the frangible capsule 171. Device 105 includes a main housing 151 designed with both an open top and an open bottom, as shown. Permanently inserted into the open top of main housing 151 is a dosage dispensing head 161, with release tube 165 and control valve 153. Dosage dispensing head 161 has a downward hemispherical end 163 for puncturing the top 173 (e.g., a foil top) of capsule 171. A circular platform or dual protrusions, such as platform 167, serves as a finger grip and is attached to main housing 151. Capsule 171 may be permanently installed in main housing 151, or it may be removably placed therein so that subsequent capsules may be inserted, the former being a monodose and the latter being a multidose device.

Further, capsule 171 may be fully frangible, but is preferably so only at its top 173. Capsule 171 could have different shape, such as a hemispherical bottom to correspond to the shape of the end 163 of the dosage dispensing head 161. Or both could have other shapes and be the same or different, e.g., a chisel shaped end/bottom. Plunger 157 has a sealed piston 159 at its distal end and a widened finger rest at its proximal end. Plunger 157 may be inserted at its distal end permanently or removably, and its piston 159 may be any shape, but is preferably the same or similar to the bottom of the capsule. The piston 159 is used to drive the capsule 171 into breaker end 163, as shown sequentially in FIGS. 11, 12 and 13. In FIG. 11, a user's thumb and first two fingers are shown embracing the plunger 157 and the platform 167, respectively. By placing the device 150 in a desired nasal cavity and pushing plunger 157 upwardly while holding the device steady, and while the user holds his/her breathe, the frangible top 173 is broken and the gas/liquid medicine begins release from the device 150 (FIG. 12). The medicine is nearly fully expended by the time the plunger 157 is pushed maximally and the top 163 is near or at the bottom of the capsule 171 (FIG. 13), to deliver the medicine to the user effectively.

Figures 14, 15:
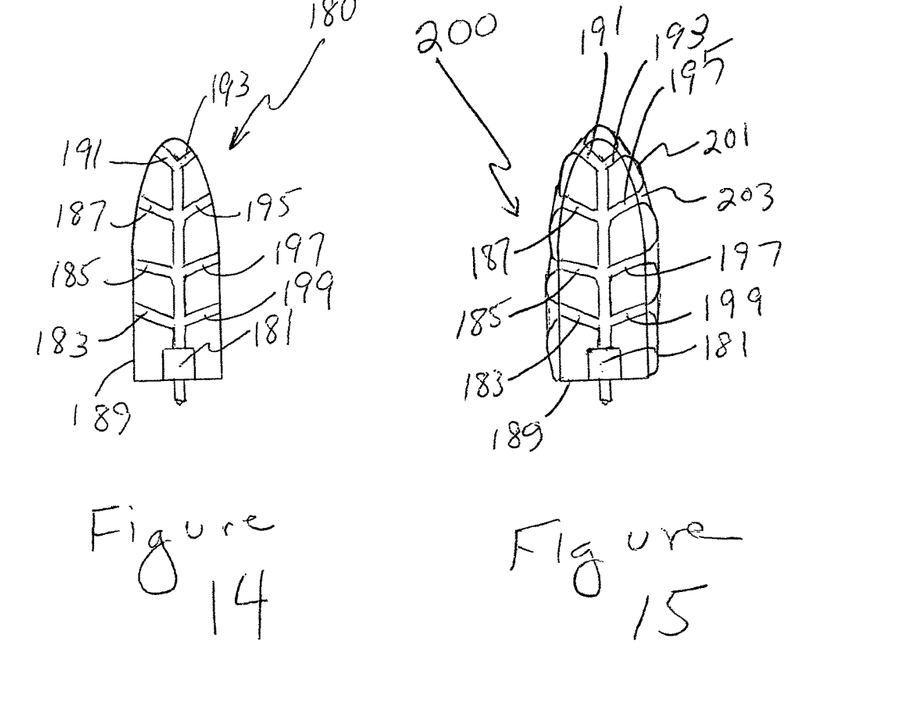
FIGS. 14 and 15 show alternative types of low flow rate dosage dispenser heads that may be used in present invention devices, one showing multiple release ports and the other showing multiple release ports with a soft contact sheath; and, FIG. 16 is a graphic representation showing present invention dosages that are cleansing biofilms and killing bacteria after one hour versus regular saline treatment and no treatment.

FIGS. 14 and 15 show alternative types of dosage dispenser heads that may be used in present invention device one has multiple release ports and the other has multiple release ports with a soft contact sheath. FIG. 14 shows a cut front view of one dosage dispenser head 180 that may be used in conjunction with a present invention device. It includes a control valve 181 to regulate release of medicine to be within the proscribed ranges set forth above. Upstream from control valve 181 is a main flow channel 183 with branches 185, 187, 189, 191, 193, 195, 197 and 199 to show a diverse multiport manifold head for diverse. This dosage dispensing head will direct the gas/liquid medicine in many directions simultaneously to more evenly and quickly coat the sinus cavity wall.

FIG. 15 shows a similar present invention dosage dispensing head 200, but with a soft pad for nasal wall comfort. This pad does not cover the ports and may be made of soft pervious or impervious materials such as various foams or skins. Alternatively, they may be previous and cover the parts so as to create wetting foams or sponges to effect broad based medicine placement in the nasal cavity.

In order to show the unexpected results of the present invention saline/carbon dioxide/carbonic acid (with or without additional active additives), consumer testing was conducted and very effective results were achieved. More than 85% in one set of testing and more than 90% in another favored the product. Only one testing consumer experienced slight stinging and no one experienced severe stinging as had occurred with carbon dioxide gas treatments as proscribed by the Capnia prior art to Rasor et al cited above. Additionally, biofilm testing was conducted to test the efficacy of the present invention.

Figure 16:
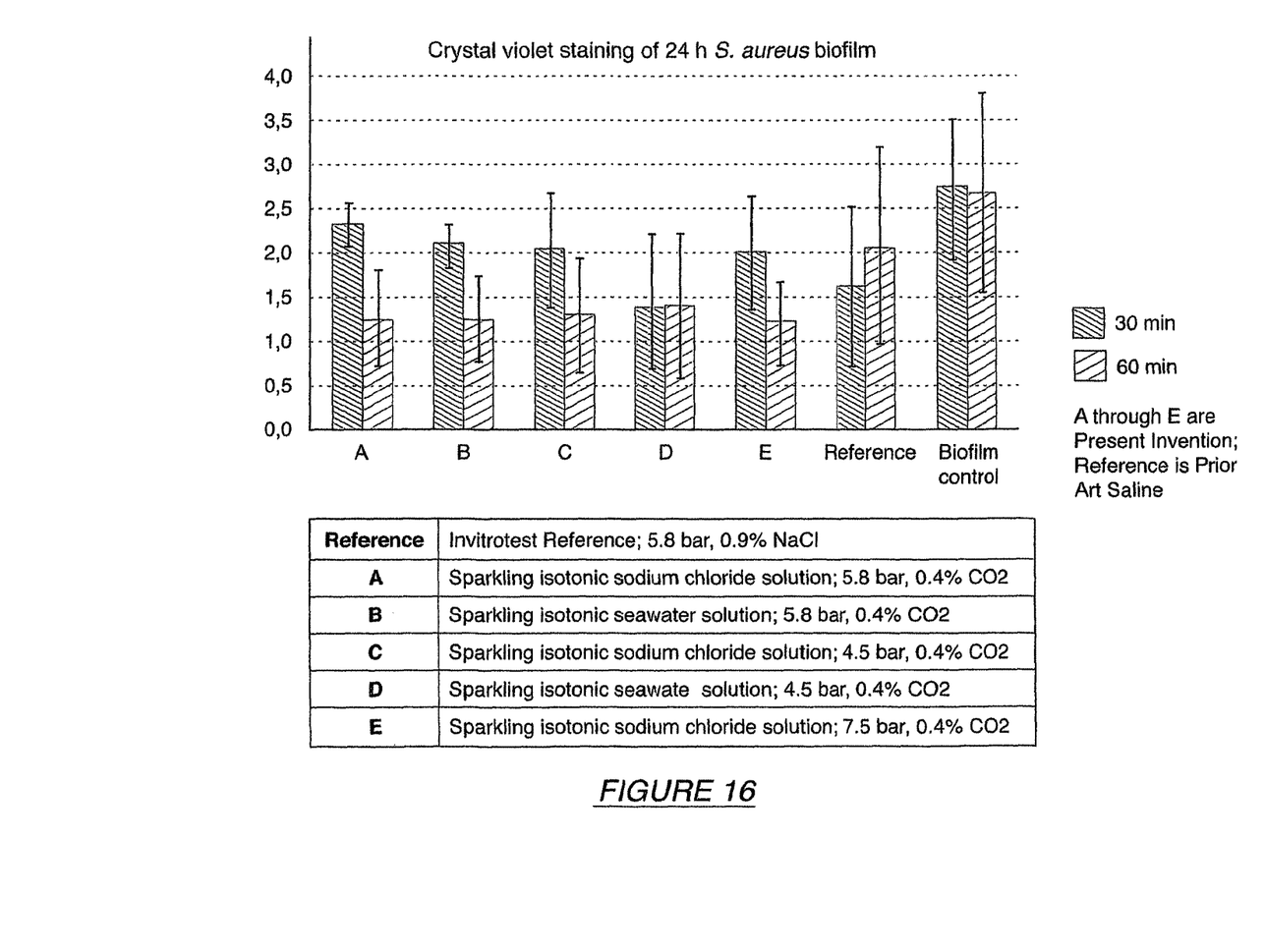

FIG. 16 shows comparative graph bars for present invention sparkling saline products A, B, C, D and E, and for a reference product (conventional prior art saline without the carbon dioxide and carbonic acid of the present invention). The tests were performed by an independent testing lab and consistent biofilms (normalized to match) of staph bacteria (24 hour growth *s. aureus* biofilm). Identical spays of present invention products A through E and the Reference Prior Art saline (0.9% isotonic) were used in the experiment. The solid bars represent relative populations of the bacteria one half hour after treatment, and the dotted diamond bars represent relative populations of the bacteria after one hour. As can be seen, all of the present invention products A through E continued to kill or remove the bacterial threat after one hour and reduced bacterial population after one half hour and after one hour significantly as compared to the end bars (biofilm control, untreated). Further, using the Prior Art Saline, the population of bacteria rose significantly after one hour as compared to one half hour. Thus, saline does not appear to have any continuing efficacy after its mechanical cleansing, whereas the present invention products were still maintaining or lowering the low population of bacteria. In addition, color photographs of these samples showed significant browning of the otherwise live green colored bacteria, further supporting that the bacteria was not only removed by the present invention, but also partially destroyed biologically. These results are even more surprising; the present invention $CO_2$ levels are much lower than the proscribed prior art Rasor et al indicated levels of $CO_2$, yet significant efficacy has been achieved, as evidenced by both the consumer use testing and the laboratory testing.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A releasable nasal treatment delivery device for mixed carbon dioxide and saline for treating head ailments in a patient in need thereof, comprising:
   a) a main housing having a proximal and a distal end and having a hollow central area containing a releasable nasal treatment dosage that includes a saline fluid and gaseous carbon dioxide, wherein said gaseous carbon dioxide is dissolved in said saline fluid;
   b) a dosage dispenser head located at said distal end of said main housing, said dosage dispenser head having at least one flow channel for movement of said dosage from said main housing through said dosage dispenser head and externally of said dosage dispenser head;
   c) a dosage release control component located between said main housing and said dosage dispenser head adapted to permit flow of the dosage comprising said saline fluid and said gaseous carbon dioxide from said main housing and through said dosage dispenser head in response to increased pressure against said dosage release control component wherein said permitted flow has controlled release at a flow rate of less than 1 cubic centimeter per second and wherein said flow rate is a total flow rate of said dosage;
   d) a pressure-changing moveable component located on said main housing;
   wherein, when said dosage dispenser head of said device is placed in a nasal cavity and said pressure-changing moveable component is activated by movement toward said dosage, said dosage is at least partially forced through said dosage release control component at the permitted flow rate and through said dosage dispenser head for application of said dosage to a nasal cavity wall.

2. The releasable nasal treatment delivery device of claim 1, wherein said dosage release control component is selected from the group consisting of a frangible member, a puncturable member and a one-way valve.

3. The releasable nasal treatment delivery device of claim 1, which further comprises:
   a nose guard flange connected to and extending from at least one of said main housing and said dosage dispenser head.

4. The releasable nasal treatment delivery device of claim 1, wherein said main housing is an open ended tube with said dosage release control component and said dosage dispenser head located at said distal end of said main housing and said pressure-changing moveable component is located at said proximal end of said main housing.

5. The releasable nasal treatment delivery device of claim 4, wherein said pressure-changing moveable component is a flexible squeeze member and a seal float.

6. The releasable nasal treatment delivery device of claim 4, wherein said pressure-changing moveable component is a push-up piston.

7. The releasable nasal treatment delivery device of claim 4, wherein at least a portion of said tube is flexible and constitutes said pressure-changing moveable component.

8. The releasable nasal treatment delivery device of claim 1, wherein said flow rate is greater than 0.01 and less than 1 cubic centimeter per second.

9. The releasable nasal treatment delivery device of claim 1, wherein said flow rate is greater than 0.08 and less than 1 cubic centimeter per second.

10. The releasable nasal treatment delivery device of claim 1, wherein said flow rate is greater than 0.1 and less than 1 cubic centimeter per second.

11. A method of treating head ailments in a patient in need thereof utilizing a nasal treatment delivery device containing dissolved carbon dioxide and saline fluid, which comprises:

a) providing the releasable nasal treatment delivery device of claim 1; and, b) directing at least a portion of the nasal treatment dosage of the device of claim 1 to at least one nasal cavity of said patient through said dosage dispenser head.

12. The method of claim 11 wherein said dosage release control component of the releasable nasal treatment delivery device of claim 1 is set to deliver a flow rate greater than 0.01 and less than 1 cubic centimeter per second.

13. The method of claim 11, wherein said dosage release control component of the releasable nasal treatment delivery device of claim 1 is set to deliver a flow rate greater than 0.08 and less than 1 cubic centimeter per second.

14. The method of claim 11, wherein said dosage release control component of the releasable nasal treatment delivery device of claim 1 is set to deliver a flow rate greater than 0.1 and less than 1 cubic centimeter per second.

* * * * *